(12) United States Patent
Shoji

(10) Patent No.: US 7,360,396 B2
(45) Date of Patent: Apr. 22, 2008

(54) GAS SENSOR AND FUEL CELL SYSTEM AND AUTOMOBILE EMPLOYING THE SAME

(75) Inventor: Rihito Shoji, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 220 days.

(21) Appl. No.: 10/595,020

(22) PCT Filed: Apr. 12, 2005

(86) PCT No.: PCT/JP2005/007061

§ 371 (c)(1),
(2), (4) Date: Dec. 19, 2005

(87) PCT Pub. No.: WO2005/100966

PCT Pub. Date: Oct. 27, 2005

(65) Prior Publication Data

US 2006/0169024 A1 Aug. 3, 2006

(30) Foreign Application Priority Data

Apr. 15, 2004 (JP) ............................. 2004-120145

(51) Int. Cl.
*G01N 7/00* (2006.01)
*G06F 19/00* (2006.01)

(52) U.S. Cl. .................. 73/31.05; 73/25.04; 73/29.01; 73/29.05

(58) Field of Classification Search ................. 73/23.2, 73/23.31, 25.04, 25.05, 29.01, 29.05, 31.05
See application file for complete search history.

(56) References Cited

FOREIGN PATENT DOCUMENTS

| JP | H08/101156 A | | 4/1996 |
|---|---|---|---|
| JP | 2003-098147 A | * | 4/2003 |
| JP | 2004/028716 A | | 1/2004 |
| JP | 2004/037235 A | | 2/2004 |

OTHER PUBLICATIONS

International Search Report of PCT/JP2005/007061.

* cited by examiner

*Primary Examiner*—Daniel S Larkin
(74) *Attorney, Agent, or Firm*—RatnerPrestia

(57) ABSTRACT

In a gas sensor, at least three levels of current are supplied to a heating element successively in a step-like manner for a predetermined time period. An arithmetic unit receives both-end voltages of the heating element for the respective current after elapse of the predetermined time period and calculates temperature from the both-end voltage of the heating element obtained when the lowest current flows. Then, the arithmetic unit corrects the both-end voltages of the heating element using the calculated temperature, a zero-point correction equation and a sensitivity correction equation to obtain respective standardized output values. Subsequently, the arithmetic unit calculates humidity based on the difference between the standardized output values, and corrects the standardized outputs based on the calculated humidity and humidity correction equations. By this method, the arithmetic unit calculates concentration of detection target gas.

19 Claims, 12 Drawing Sheets

GAS SENSOR AND FUEL CELL SYSTEM AND AUTOMOBILE EMPLOYING THE SAME

THIS APPLICATION IS A U.S. NATIONAL PHASE APPLICATION OF PCT INTERNATIONAL APPLICATION PCT/JP2005/007061, filed Apr. 12, 2005.

TECHNICAL FIELD

The present invention relates to a gas sensor for detecting humidity and concentration of gas mixed with the atmosphere containing moisture, and to a fuel cell system and an automobile including the gas sensor.

BACKGROUND ART

Recently, great progress has been made in the development of a fuel cell, which is expected as one of the most effective solutions to the environmental problems. Particularly, a fuel cell using solid polymeric film as electrolyte has been the mainstream in the current fuel cell development since the solid polymeric film having the operation temperature of as low as 80° C. is easy to be treated. This fuel cell uses hydrogen fuel, and thus requires a gas sensor for detecting hydrogen as the safety measures for preventing hydrogen leak.

A gas sensor having been currently proposed utilizes such characteristics of hydrogen that its thermal conductivity is extremely larger than those of other gases and detects variations in thermal conductivity due to the existence of hydrogen from temperature variations of a heating element. When hydrogen exists in the air, for example, larger quantity of heat is robbed from the heating element compared with the case where only the air exists. The temperature of the heating element therefore varies in accordance with the concentration of hydrogen, and those variations in temperature are electrically detected as changes in the resistance value of a temperature detecting element.

The heating element of the gas sensor, which is also used as the temperature detecting element, is formed by a platinum thin-film resistor. The platinum thin-film resistor, which has a thin-film structure, is manufactured using semiconductor micro machining technique, and is thus capable of producing minute heating elements. Thus, the power consumption decreases, and the response speed of the gas sensor increases. The gas sensor having this structure has been disclosed in JP-A-8-101156, for example.

When this type of gas sensor is used for detection of a hydrogen leak, a problem arises if moisture is contained in hydrogen as detection target gas. The resistance value of the heating element varies in accordance with the concentration of hydrogen if no moisture is contained. However, the resistance value also varies with the existence of moisture if it is contained, and it is therefore impossible to make distinction between changes caused by hydrogen, by moisture, and by coexistence of those.

In order to overcome this problem, the conventional gas sensor described above varies current which flows in the heating element formed by the platinum thin-film resistor. In this structure, the output voltage of the heating element changes in accordance with the degree of reaction, and the voltages at the both ends of the heating element obtained when respective levels of current flow therein are substituted in estimate equations established in advance and the equations are simultaneously calculated. Then, the quantities of the atmospheric gases, that is, the concentrations of the respective gases are calculated from the solutions of the estimate equations.

Basically, the gas concentrations of a plurality of constituents can be obtained by this method. However, a problem occurs when hydrogen substantially saturated with moisture leaks in the atmosphere at a temperature of nearly 80° C. in such a case as leakage detection from a fuel cell. When variations in the thermal conductivities of the respective gas constituents are expressed by linear equations or in such applications where those variations are detected only in the range of linear equations, the gas concentrations can be calculated using Chebyshev's orthogonal polynomial. In case of the fuel cell, however, it is estimated that a larger quantity of vapor than that of hydrogen is contained. In this condition, the thermal conductivities of the mixture family have non-linear characteristics which are always quadratic or have higher degrees, and rise as humidity increases, exhibit a peak, and then decrease. Thus, complicated calculations are required when solutions are obtained only from the simultaneous estimate equations. Moreover, since a plurality of solutions correspond to humidity, it is impossible to determine one value as humidity. As a result, it is also impossible to obtain one value as concentration of hydrogen.

SUMMARY OF THE INVENTION

A gas sensor according to the invention includes: a heating element which contacts detection target gas mixed with the atmosphere containing moisture; a power source device for supplying electric current to the heating element; and a voltmeter for measuring voltage at both ends of the heating element. The gas sensor further includes an arithmetic unit for calculating humidity and concentration of the detection target gas based on output voltage from the voltmeter and outputting the calculated values. The arithmetic unit commands the power source device to supply at least three levels of current to the heating element successively in a step-like manner for a predetermined time period. Then, the arithmetic unit receives the both-end voltages of the heating element for the respective current after elapse of the predetermined time period.

Thereafter, the arithmetic unit corrects the both-end voltages of the heating element when current other than the lowest current is obtained. Both a zero-point fluctuation correcting equation and a sensitivity fluctuation correcting equation utilize the both-end voltage of the heating element. This occurs when the lowest current flows and concentration of the detection target gas is known, so as to obtain respective standardized output values. Subsequently, the arithmetic unit calculates humidity using a humidity correlation function which uses parameters of the difference between the standardized output values and the both-end voltage of the heating element when the lowest current flows. Thereafter, the arithmetic unit corrects the zero-point fluctuation and sensitivity fluctuation relative to the humidity thus obtained using two humidity correction value correlation functions which use parameters of the difference between the standardized output values and the both-end voltage of the heating element when the lowest current flows to obtain the concentration of the detection target gas. By this method, the gas sensor according to the invention can detect humidity and concentration of detection target gas with high accuracy.

Figure 1:
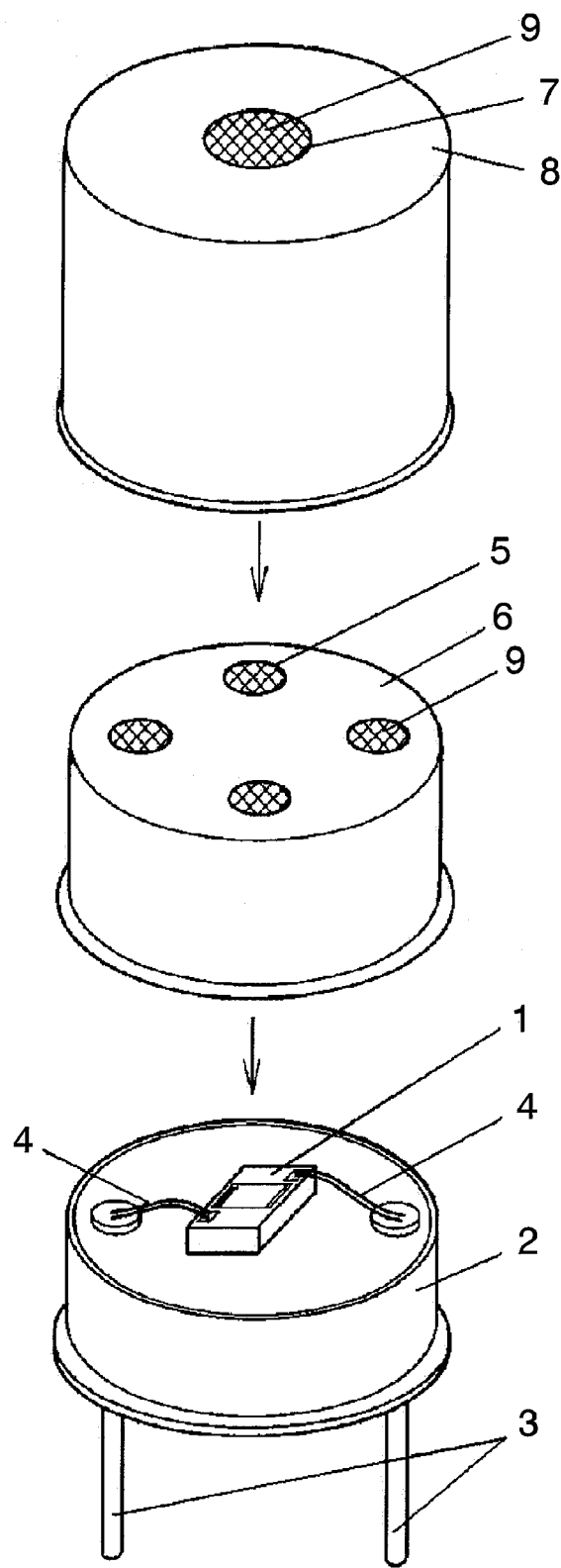
FIG. 1 is a perspective view of a disassembled gas detection section of a gas sensor in an embodiment according to the invention.

REFERENCE MARKS IN THE DRAWINGS 1 heating element
2 base
3 pin
4 wire
5 inner hole
6 inner can
7 outer hole
8 outer can
9 net
10 pedestal
11 heating body
12 land
13 concavity
16 detection section
17 detection circuit
18 container
19 pickup cable
20 container lid
21 moist-resistant resin
22 gas intake opening
23 screw
24, 113 gas sensor
25 constant current source
26 voltmeter
27 arithmetic unit
51 hydrogen tank
52 cutoff valve
53 hydrogen humidifier
54, 110 fuel cell
55 air compressor
56 air humidifier
57 fuel cell control circuit
58 housing
59 alarm
60 ventilation fan
101 main body
102 vehicle compartment
103 hydrogen tank accommodating section
104 driving means accommodating section
105 under-floor section
106 tank
107 outside tank
108 inside tank
109 motor
111 tire
112 steering wheel

DETAILED DESCRIPTION OF THE PREFERRED EMBODIMENT

An embodiment according to the invention is hereinafter described with reference to the appended drawings. In the following description, it is assumed that detection target gas is hydrogen.

Figure 2A:
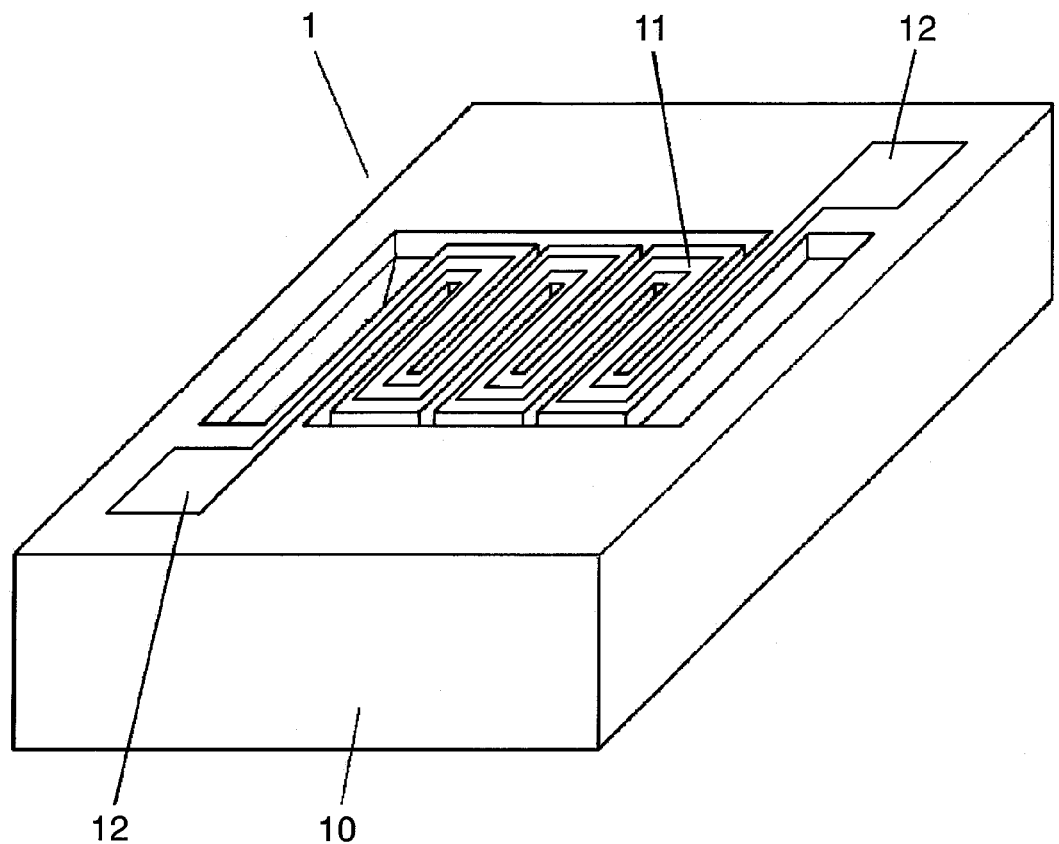
FIG. 2A is a perspective view schematically illustrating a heating element of the gas sensor in the embodiment according to the invention.
Figure 2B:
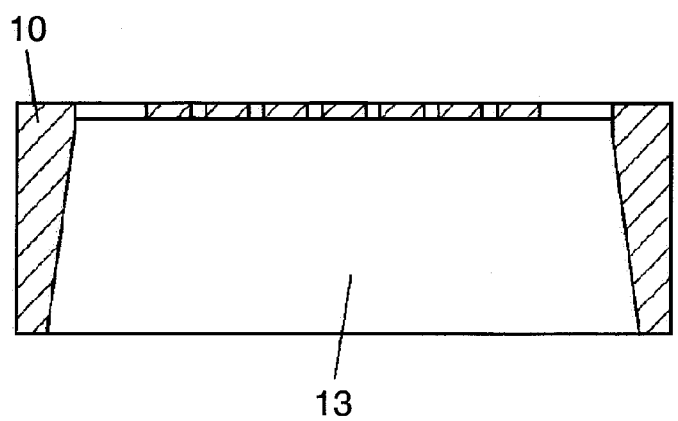
FIG. 2B is an enlarged cross-sectional view of the heating element of the gas sensor in the embodiment according to the invention.
Figure 3:
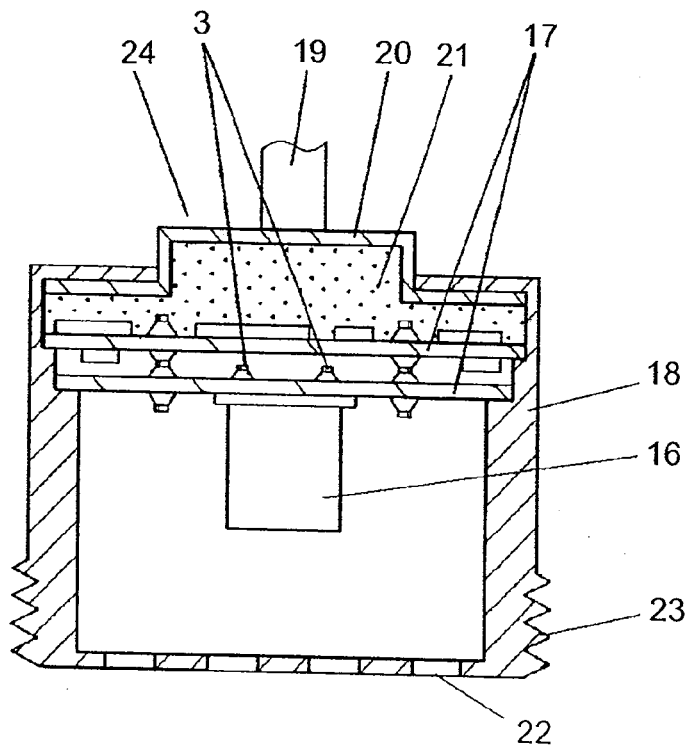
FIG. 3 is a cross-sectional view schematically illustrating the gas sensor in the embodiment according to the invention.

FIG. 1 is a perspective view illustrating a disassembled gas detection section of a gas sensor in an embodiment according to the invention. FIG. 2A is a perspective view schematically illustrating a heating element of the gas sensor in the embodiment according to the invention. FIG. 2B is an enlarged cross-sectional view of the heating element of the gas sensor in the embodiment according to the invention. FIG. 3 is a cross-sectional view schematically illustrating the gas sensor in the embodiment according to the invention.

As illustrated in FIG. 1, heating element 1 is fixed on base 2. A pair of pins 3 penetrate through base 2. Two pairs of wires 4 made of metal connect the top surfaces of pins 3 and heating element 1. Two pairs of wires 4 are equipped so that at least one of the pair of wires 4 can be kept connected with pin 3 and heating element 1 when the other of the pair is broken. This structure allows the gas sensor to be successively used, which enhances its reliability. Base 2 is covered by inner can 6 having four inner holes 5, and inner can 6 is further covered by outer can 8 having one outer hole 7, thereby constituting a dual can structure. Inner holes 5 and outer hole 7 are disposed offset from each other when attached to base 2 so as not to be opposed to each other. In this structure, gas does not directly reach heating element 1, so that the flow amount of the target gas does not greatly affect outputs of the gas sensor. Base 2, inner can 6 and outer can 8 are fixed to one another by resistance welding. Nets 9 made of metal, such as stainless steel, are secured to inner holes 5 and outer hole 7.

As illustrated in FIGS. 2A and 2B, heating element 1 has pedestal 10 made of silicone and heating body 11 made of platinum thin film. Heating body 11 is provided in the zigzag shape on the surface of concavity 13 which is formed into an extremely thin film having a thickness of approximately ten micrometers by micromachining method. This structure allows the heat capacity of heating body 11 to be extremely small. Lands 12 with which wires 4 are bonded are formed on both ends of heating body 11. A not shown insulating layer made of silica is provided on the lower surfaces of heating body 11 and lands 12. Also, a not shown protective layer made of silica is provided on the upper surface of heating body 11.

Detection section 16 is formed by mounting heating element 1 on the case constituted by base 2, inner can 6 and outer can 8 shown in FIG. 1. As illustrated in FIG. 3, detection section 16 is electrically and mechanically connected by inserting pins 3 into detection circuit 17 and soldering pins 3 thereto. Detection circuit 17 is inserted into container 18. Container lid 20 through which pickup cable 19 connected with detection circuit 17 is inserted in advance is attached to container 18. Moisture-resistant resin 21 is injected through an injection opening (not shown) formed on container lid 20 into the entire space between detection circuit 17 and container lid 20, and is then hardened therein. The space between container 18 and container lid 20 is caulked after moisture-resistant resin 21 is injected to and hardened in the space.

Gas intake openings 22 are provided on the bottom surface of container 18. Screw 23 used for attaching the sensor is formed on the side of container 18. Assembly of gas sensor 24 is thus completed using the above-described components.

Next, attachment examples of the gas sensor are discussed with reference to FIGS. 4 and 5.

Figure 4:
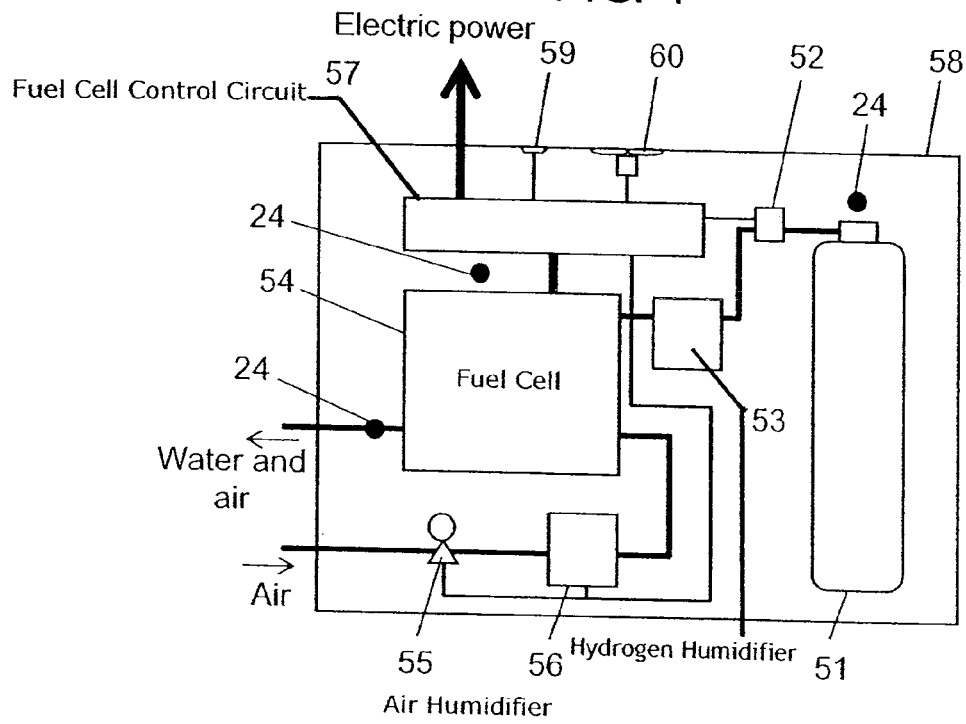
FIG. 4 is a block diagram schematically showing the gas sensor in the embodiment according to the invention attached to a stationary type fuel cell system.
Figure 5:
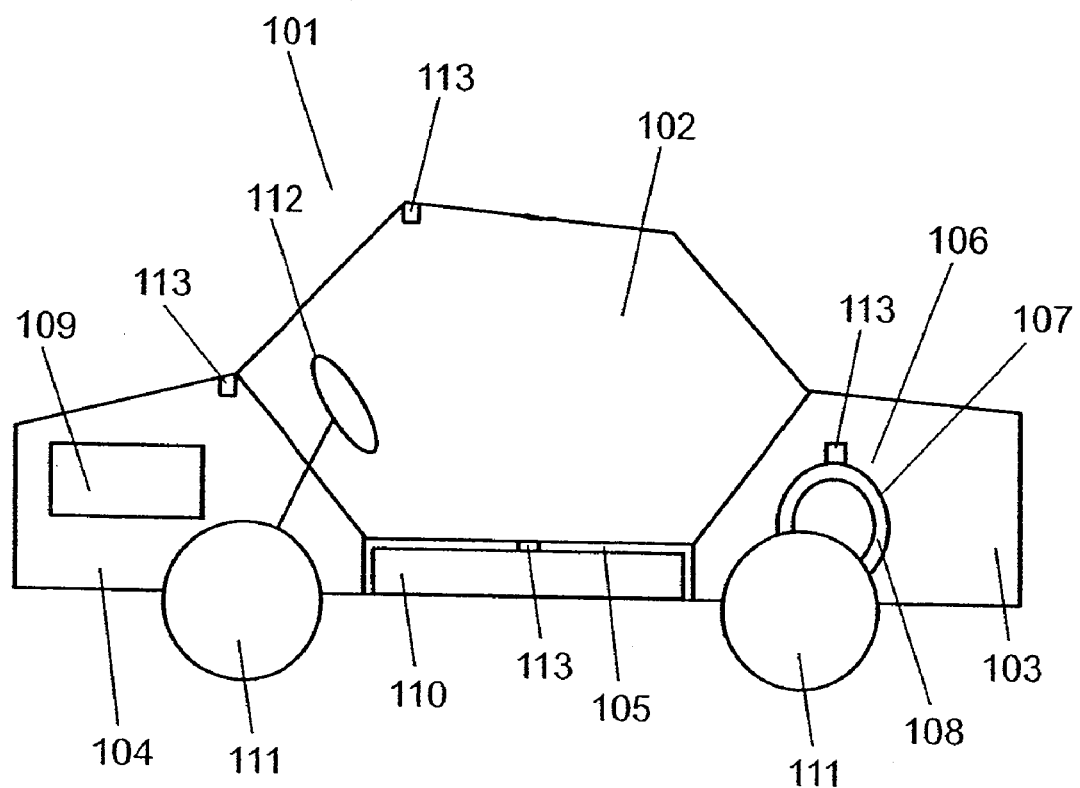
FIG. 5 is a cross-sectional view schematically illustrating a structure of a fuel cell automobile including the gas sensor in the embodiment according to the invention.

FIG. 4 is a block diagram schematically showing the gas sensor in the embodiment according to the invention which is attached to a stationary type fuel cell system. FIG. 5 is a cross-sectional view schematically showing a structure of a fuel cell automobile including the gas sensor in the embodiment according to the invention.

Initially, a fixed polymeric film electrolyte type fuel cell system is explained as an example of the stationary type fuel cell system. As illustrated in FIG. 4, hydrogen contained in hydrogen tank 51 is introduced through cutoff valve 52 into hydrogen humidifier 53, where moisture for preventing a solid polymeric film provided within the fuel cell from being dried is given. The humidified hydrogen is then guided toward the hydrogen pole of fuel cell 54. On the other hand, air necessary for generating electricity is humidified by air humidifier 56 using air compressor 55, and is then introduced toward the air pole of fuel cell 54. This structure allows fuel cell 54 to generate electricity, and to supply electric power through fuel cell control circuit 57 to the outside as shown by a bold line. Water produced as a by product of electricity generation is discharged with air from fuel cell 54 to the outside. In the case of are forming type fuel cell system, hydrogen tank 51 is replaced with a reformer.

The fuel cell system having this structure is accommodated within housing 58. The gas sensors for detecting a hydrogen leak are disposed in the vicinities of hydrogen tank 51 and fuel cell 54, within the air discharge piping of fuel cell 54, and other positions, as shown by black circles in FIG. 4. When the gas sensors other than those positioned within the air discharge piping detect a hydrogen leak, fuel cell control circuit 57 closes cutoff valve 52 to stop hydrogen supply to fuel cell 54 and then actuates alarm 59 and ventilation fan 60. When the concentration of hydrogen detected by the gas sensor, disposed within the air discharge piping, exceeds a specified value (for example, 2%, which is half of 4% as the explosion limit of hydrogen to secure safety), fuel cell control circuit 57 operates air compressor 55 and increases the discharge airflow amount such that the concentration of hydrogen becomes lower. Moreover, fuel cell control circuit 57 detects lowering of humidity in the air due to the increase in the airflow amount based on the humidity output from the gas sensor, and controls air humidifier 56 such that humidity is kept at a predetermined value.

Next, a fuel cell automobile is explained. As illustrated in FIG. 5, main body 101 of the automobile includes vehicle compartment 102, hydrogen tank accommodating section 103, driving means accommodating section 104, and under-floor section 105, all of which are combined. Hydrogen tank accommodating section 103 has tank 106 for containing hydrogen. Tank 106 has a dual structure constituted by outside tank 107 and inside tank 108 so as to secure safety preventing a hydrogen leak especially at the time of collision. Inside tank 108 contains hydrogen. Driving means accommodating section 104 has motor 109 for driving main body 101. Under-floor section 105 has fuel cell 110.

Hydrogen supplied from tank 106 is converted into electrical energy by fuel cell 110 disposed in under-floor section 105. The electrical energy thus obtained is transmitted to motor 109 to drive tires 111. The steering direction of tires 111 is controlled by steering wheel 112 disposed within vehicle compartment 102.

In the automobile having this structure, gas sensors 113 are provided in respective positions. More specifically, gas sensor 113 equipped in vehicle compartment 102 is located in the front region of the ceiling which is the uppermost position in vehicle compartment 102. Gas sensor 113 equipped in hydrogen tank accommodating section 103 is located at the uppermost position of outside tank 107 since tank 106 has the dual structure. Gas sensor 113 equipped in driving means accommodating section 104 is located at the rear end of the bonnet which is the uppermost position in driving means accommodating section 104. Gas sensor 113 equipped in under-floor section 105 is located at the uppermost position of under-floor section 105. Additionally, a not shown gas sensor is provided within the air discharge piping of fuel cell 110 similarly to the case shown in FIG. 4.

When any of these gas sensors detects a hydrogen leak, fuel cell control circuit 57 cuts off the supply source of hydrogen and stops supply of hydrogen to the fuel cell in the same manner as the case explained with reference to FIG. 4. Also, alarm 59 gives a warning and ventilation fan 60 ventilates the inside of main body 101. In addition, gas sensor 113 equipped inveigle compartment 102 detects humidity, and controls the air conditioner provided in a certain region of vehicle compartment 102 such that the inside of vehicle compartment 102 has optimum humidity.

Next, the operation of the gas sensor is discussed.

Figure 6:
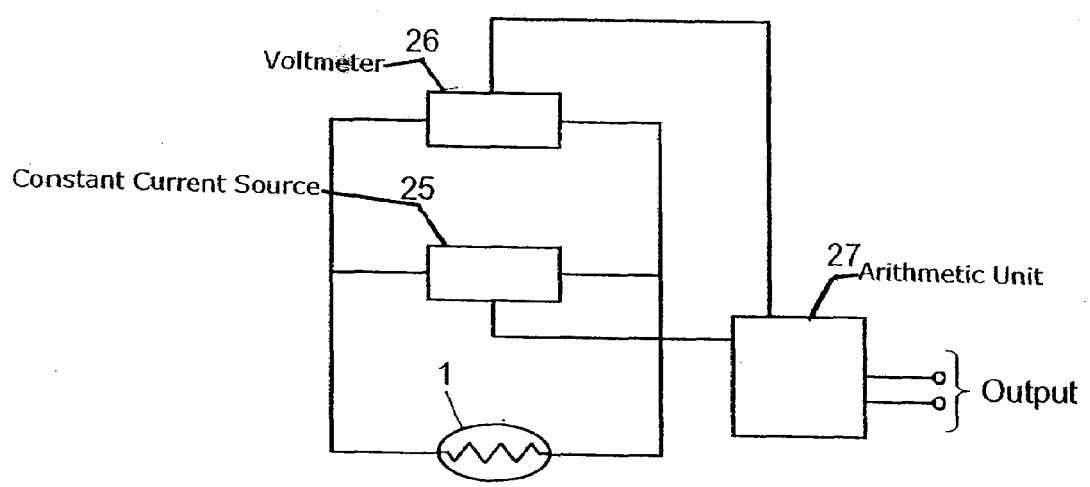
FIG. 6 is a circuit diagram schematically showing the gas sensor in the embodiment according to the invention.

FIG. 6 is a circuit diagram schematically illustrating a circuit structure of the gas sensor in the embodiment according to the invention. As illustrated in FIG. 6, constant current source 25 as a power source device is connected to heating element 1. Voltmeter 26 for measuring voltage at both ends of heating element 1 is connected in parallel with constant current source 25. Constant current source 25 and voltmeter 26 are further connected to arithmetic unit 27 having a microcomputer. Arithmetic unit 27 controls constant current source 25 and performs predetermined calculations based on the outputs from voltmeter 26 to output the concentration of hydrogen and humidity.

Figure 7:
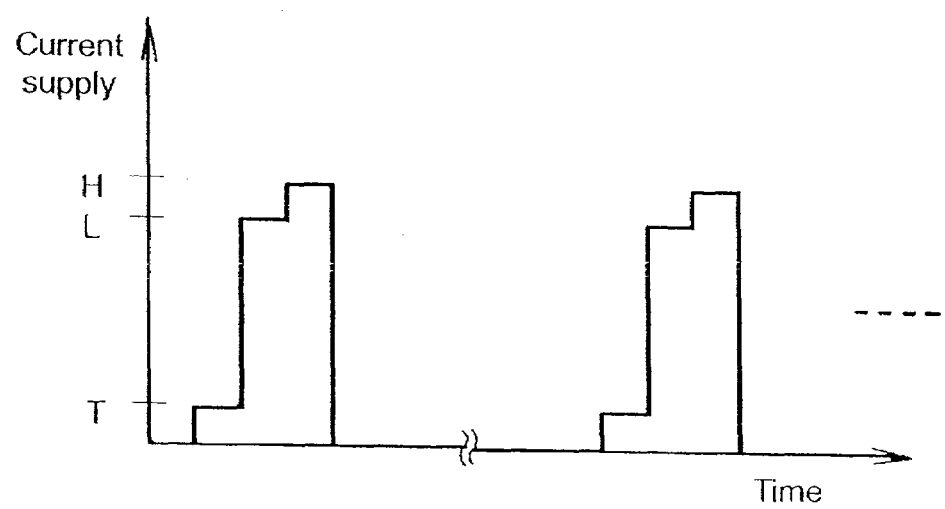
FIG. 7 schematically shows a waveform of current supplied to the heating element of the gas sensor in the embodiment according to the invention.

FIG. 7 schematically shows a waveform of current supplied to the heating element of the gas sensor in the embodiment according to the invention. As illustrated in FIG. 7, constant current source 25 supplies three levels of current to heating element 1 successively in a step-like manner for a predetermined time period based on the commands given from arithmetic unit 27. More than three levels of current may be supplied. In this embodiment, the initial current value (first value) is 1 mA or smaller, the second current value (second value) is 7 mA, and the third current value (third value) is 7.5 mA, where current flows for 0.1 second at each level. After current flow at the third level is finished, arithmetic unit 27 stops current supply to heating element 1 and waits for 1.7 second. During this period, heating element 1 is cooled down to the ambient temperature. One cycle of this current control is repeated at intervals of two seconds. These values of current and time established herein are only an example obtained from heating element 1 in this embodiment, and the invention is not limited to the specific values.

While controlling current as described above, arithmetic unit 27 receives voltages measured by voltmeter 26 immediately before switching values of current, that is, after elapse of the predetermined time period. Thus, arithmetic unit 27 receives three voltages for each cycle. These voltages are herein referred to as T value (first output value), L value (second output value), and H value (third output value) from the lowest to the highest current values.

T value corresponds to the voltage of heating element 1 which generates substantially no heat, since the value of current supplied to heating element 1 is 1 mA or smaller. In this condition, since heating element 1 corresponds to a platinum temperature sensing element, the T value representing both-end voltage of heating element 1 shows approximately the ambient temperature of heating element 1 only. Thus, substantially no change in thermal conductivity relative to gas types is detected.

The L and H values are voltages of heating element 1 when heating element 1 generates heat. In this case, voltages are obtained according to temperatures at which heat robbed from heat element 1 according to types and concentrations of gases and the ambient temperature is in equilibrium with heat generated from heating element 1. Thus, the L and H values are voltages as synthesis of parameters of the ambient temperature and the types and concentrations of gases. Obviously, the temperature of heat generated by heating element 1 is lower at the L value obtained when lower current flows than at the H value.

Figure 8:
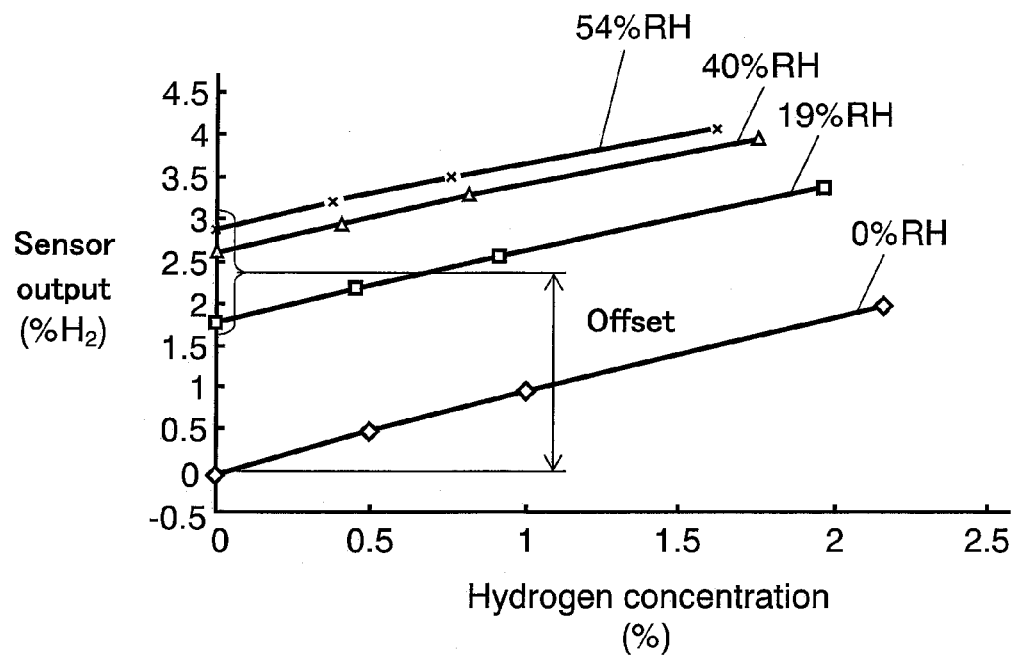
FIG. 8 shows hydrogen concentration output characteristics in a humidified condition when the heating element of the gas sensor in the embodiment according to the invention generates high-temperature heat.

Shown below is hydrogen concentration dependence in the humidified atmosphere at 80° C. at a representative value of the H value. The H values outputted under the respective hydrogen concentrations and humidity conditions are standardized. More specifically, the H value outputted when only air is supplied to the gas sensor under the non-humidified condition (0% RH: RH is relative humidity) is zero. The H value outputted when air mixed with 1% of hydrogen is supplied to the gas sensor is 1. FIG. 8 shows the results, representing hydrogen concentration output characteristics when the heating element generates high-temperature heat in the humidified condition. The horizontal axis indicates the concentration of hydrogen supplied to the gas sensor, while the vertical axis indicates the standardized sensor output (% $H_2$).

As can be seen from FIG. 8, the sensor output greatly varies relative to humidity to such an extent that the variations cannot be neglected when moisture is contained in the atmosphere. Thus, the sensor has the same level of sensitivity for the hydrogen detection and for the humidity detection. Similar conclusions can be drawn from the case of the L value. It is therefore impossible to separately detect hydrogen and humidity from the L value or the H value only. Accordingly, the following calculations are executed to output both levels.

Figure 9:
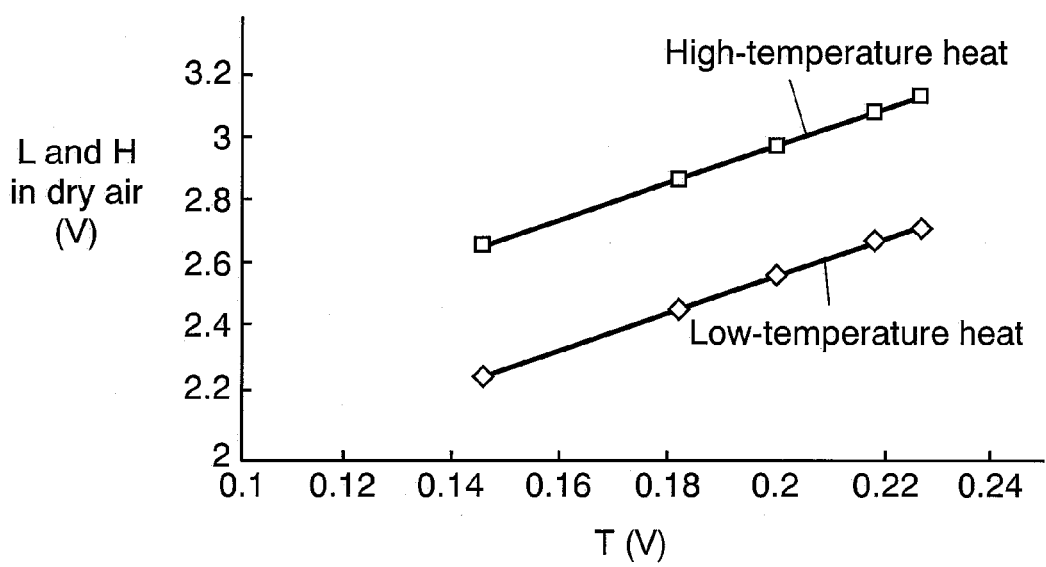
FIG. 9 shows zero-point temperature-dependence characteristics when the heating element of the gas sensor in the embodiment according to the invention generates low-temperature heat and high-temperature heat.

Generally, thermal conductivities of gases have dependence on temperature, and thus correction of the T value corresponding to the ambient temperature is carried out for the Land H values. More specifically, correction of zero point (output value when only dry air exists) is initially performed. In this correction, the temperature is varied while the dry air is being supplied to the gas sensor. Then, correction is carried out based on the T, L and H values outputted at the respective temperatures using a correction equation. FIG. 9 shows an actual output example.

FIG. 9 shows zero-point temperature-dependence characteristics when the heating element generates low-temperature heat and high-temperature heat in the gas sensor in the embodiment according to the invention. In FIG. 9, the results are plotted on the graph which has the horizontal axis indicating the T values (corresponding to the ambient temperature) and the vertical axis indicating the L and H values which are outputted when the ambient temperature is −40, 20, 50, 80, and 95° C.,. Both the L and H values vary relative to the T values corresponding to the ambient temperature, and thus obviously the zero point depends on temperature. When the zero-point correction equation for the L and H values is obtained by quadratic approximation using the method of least squares based on these results, the following relationships hold:

$$L0=-0.1708 \times T^2+6.2123 \times T+1.3174 \quad (1)$$

$$H0=-0.0349 \times T^2+6.2338 \times T+1.7232 \quad (2)$$

The proportion of effect L0 and H0 coming from the temperature dependence of the zero-point in the L and H values outputted under an arbitrary humidity and hydrogen environment are obtained by substituting the T value corresponding to the ambient temperature in the equations (1) and (2). Thus, values ZL and ZH, which are the zero-point-corrected L and H values under the arbitrary environment, are obtained by the following equations:

$$ZL=L-L0 \quad (3)$$

$$ZH=H-H0 \quad (4)$$

Since quadratic approximation is employed in equations (1) and (2), fewer correction errors occur than in the case where linear approximation is employed.

Next, sensitivity correction relative to the ambient temperature is discussed. Generally, gaseous thermal conductivity varies relative to the ambient temperature even when gas having the same concentration exists. That is, gas sensitivity of the thermal conductivity has temperature-dependence characteristics. Thus, temperatures are varied while gas as a mixture of dry air and hydrogen having a certain concentration (1% herein) is being supplied to the gas sensor, and correction is performed using a correction equation obtained based on the T, L and H values outputted at each temperature. Since the zero-point is variable in accordance with variations in temperature as described above, the zero-point-corrected values (ZL, ZH) for the L and H values are calculated in advance using the equations (3) and (4), and then the values ZL and ZH are sensitivity-corrected.

Figure 10:
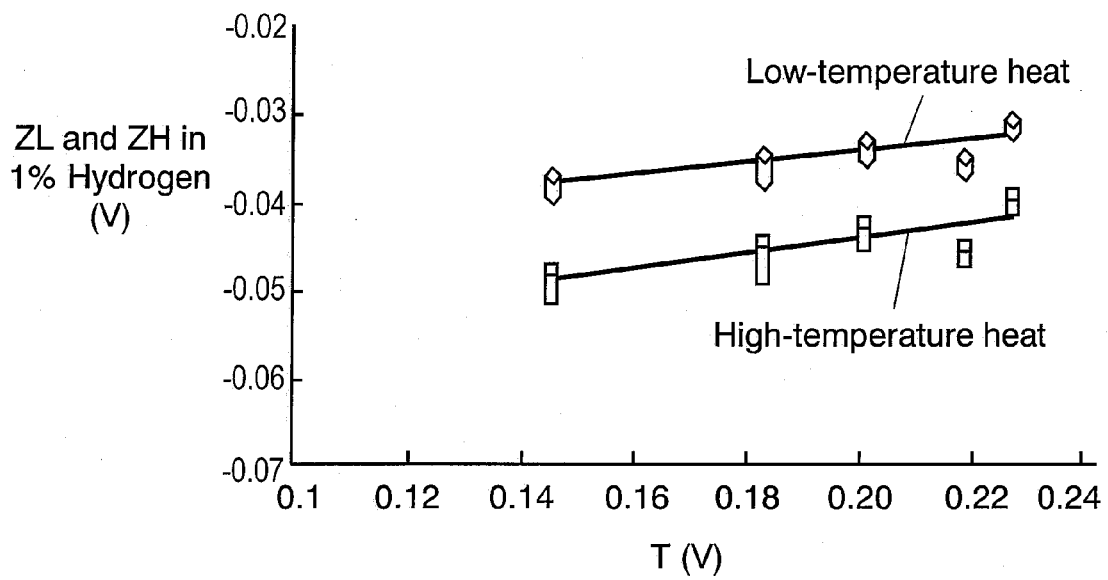
FIG. 10 shows sensitivity correction characteristics in accordance with temperature change when the heating element of the gas sensor in the embodiment according to the invention generates low-temperature heat and high-temperature heat.

FIG. 10 shows the actual temperature-dependence characteristics of the output values ZL and ZH when dry air containing 1% hydrogen is supplied(=1% hydrogen sensitivity). The ambient temperature varies in a similar manner as in the case of zero-point correction. The horizontal axis indicates the T value (corresponding to the ambient temperature), and the vertical axis indicates the ZL and ZH values. As apparent from FIG. 10, the sensitivity to 1% hydrogen has temperature-dependence characteristics. When the sensitivity correction equations for the ZL and ZH values are obtained by quadratic approximation using the method of least squares, the following relationships hold:

$$ZL1=-0.2053 \times T^2+0.1544 \times T-0.0565 \quad (5)$$

$$ZH1=-0.2656 \times T^2+0.2068 \times T-0.0745 \quad (6)$$

where ZL1 and ZH1 are sensitivity correction coefficients relative to temperature. By using these equations, the output values ZL and ZH under an arbitrary environment are sensitivity-corrected and standardized with respect to the hydrogen concentrations to obtain values KL and KH, which are calculated by the following equations:

$$KL=ZL/ZL1 \quad (7)$$

$$KH=ZH/ZH1 \quad (8)$$

By using the equations (7) and (8), the values of KL (first standardized output value) and KH (second standardized output value) are standardized to the unit of hydrogen concentration percentages (hereinafter referred to as % $H_2$). Since quadratic approximation is also employed in equations (5) and (6) similarly to the case of the zero-point correction, fewer correction errors occur than in the case where linear approximation is employed.

A method for obtaining humidity output is now explained. As indicated by offset (sensor output when hydrogen concentration is zero) shown in FIG. 8, the humidity output exhibits non-linear characteristics relative to humidity.

Figure 11:
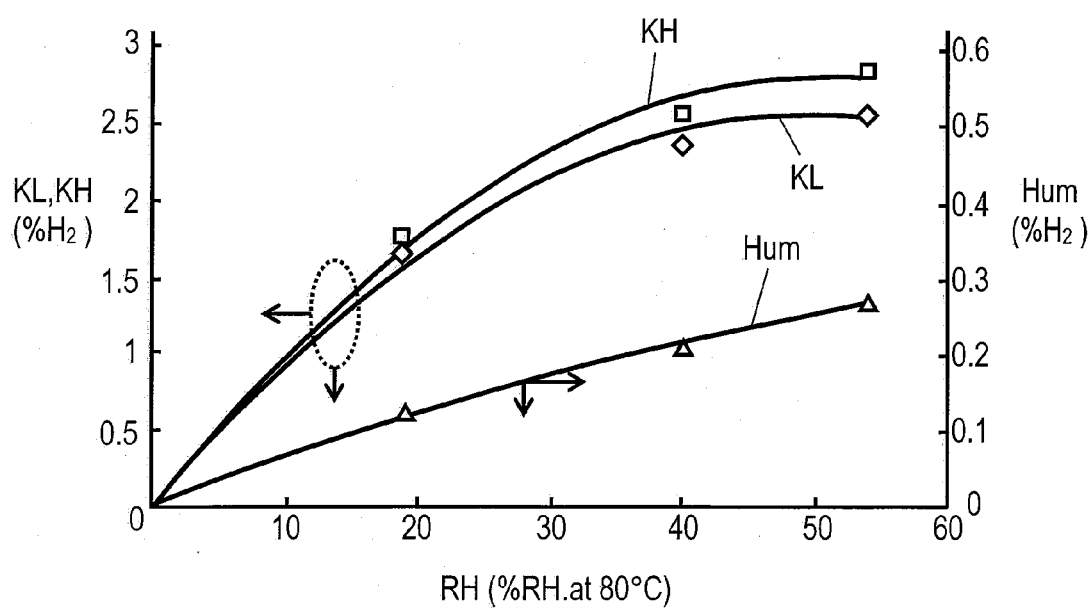
FIG. 11 shows a correlation between humidity and standardized outputs after zero-point and sensitivity corrections in the gas sensor in the embodiment according to the invention.

FIG. 11 shows a correlation between humidity and the standardized outputs after the zero-point correction and sensitivity correction in the gas sensor in the embodiment according to the invention. That is, the figure shows a correlation between the values KL and KH and relative to humidity RH in moist air at 80° C. containing no hydrogen. The horizontal axis indicates RH, while the left vertical axis indicates KL and KH. In FIG. 11, both the standardized output values KL and KH relative to the relative humidity RH exhibit non-linear characteristics having a peak. These characteristics directly represent thermal conductivity characteristics of moist air. Thus, approximation equations for the values KL and KH relative to the relative humidity RH need be expressed by equations quadratic or having higher degrees. As a result, a plurality of solutions are obtained when simultaneous equations are calculated using these approximation equations (estimation equations). It is therefore impossible to determine one value as humidity, and thus one value as hydrogen concentration.

However, when the thermal conductivity of gas mixture, such as moist air, is calculated using Sutherland-Wassiljewa type theoretical equation, the thermal conductivity varies as the temperature changes even in gas mixture having the same concentration. This is because the combining coefficients in the equation and the thermal conductivities of the net components included in the constituent gases have temperature-dependence characteristics. Thus, the humidity sensitivity varies at different temperatures of heat generated from heating element 1 even at the same humidity. This is supported by the fact that the plots of KL are different from those of KH in FIG. 11. Considering this point, the difference between the outputs (corresponding to KL and KH herein) from heating element 1 at different heat temperatures exhibits substantially linear characteristics in the range of humidity at which the gas sensor is used, when calculated using the above theoretical equation. The actual difference between KL and KH (=Hum: see the right vertical axis) as the calculated results are shown in FIG. 11. As can be seen from FIG. 11, the value Hum exhibits substantially linear characteristics relative to the relative humidity RH, which supports the theoretical calculation. From these facts, it is possible to determine one value as humidity by calculating Hum. Since Hum represents the difference between KL and KH which are standardized with respect to hydrogen sensitivity, Hum corresponds to humidity. Also, from the mathematical viewpoints, Hum corresponds to a value obtained by removing the effect of hydrogen concentration from output in an arbitrary environment.

Figure 12:
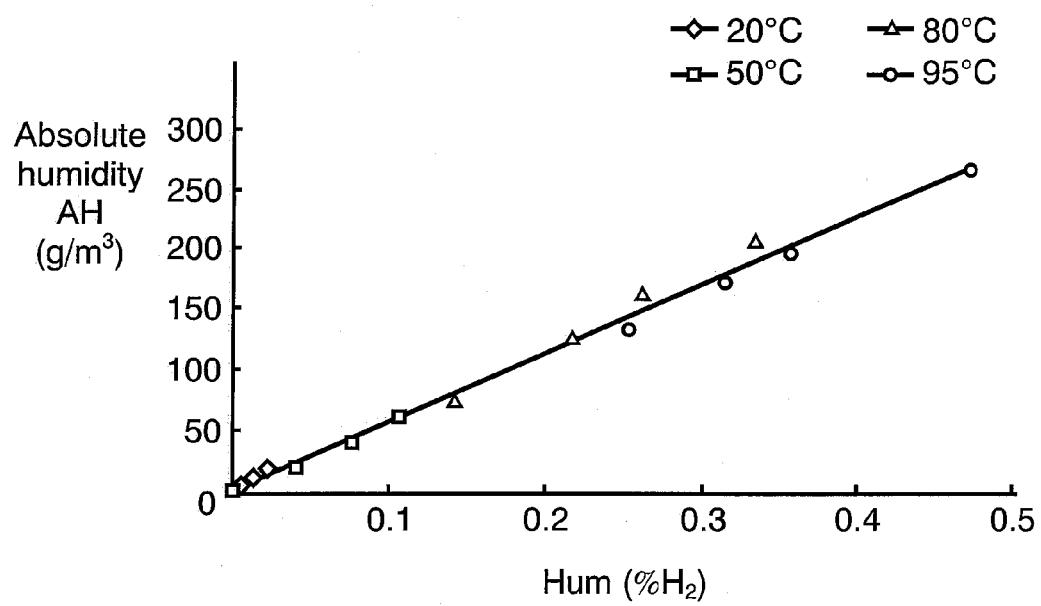
FIG. 12 shows a correlation between absolute humidity and the difference between the standardized outputs when the heating element generates low-temperature heat and high-temperature heat in the gas sensor in the embodiment according to the invention.

FIG. 12 shows a correlation between the absolute humidity and the difference between the standardized outputs when the heating element generates low-temperature heat and high-temperature heat in the gas sensor in the embodiment according to the invention. The actual Hum values are obtained and their correlations with the absolute humidity are plotted. In FIG. 12, the horizontal axis indicates the difference Hum between KL and KH (=KH−KL), while the vertical axis indicates the absolute humidity AH. The absolute humidity AH is used herein so as to indicate the humidity characteristics exhibited with variations in temperature on the same graph. As apparent from FIG. 12, the correlation between Hum and the absolute humidity AH expresses not non-linear characteristics having a peak, but substantially linear characteristics from which one value can be determined as humidity.

However, the absolute value AH obtained from Hum in FIG. 12 has great errors especially at the time of high humidity when compared with an approximate curve obtained from the respective plots using the method of least squares, because the correlation between Hum and AH varies in accordance with temperature change. Detailed examination of the characteristics of the plots at respective temperatures in FIG. 12 shows that the plots are positioned substantially on the same curve at a constant temperature. It is thus impossible to correct the values of the absolute humidity AH based on a single correction curve.

The correlation between Hum and AH varies in accordance with temperature change, because the temperature of heat generated from heating element 1 under constant-current driving varies in accordance with the ambient temperature change. When similar conditions are given to the above thermal conductivity theoretical equation and the correlation between Hum and the thermal conductivity (corresponding to AH) obtained with variance in temperature is calculated, similar results are obtained. This means that the temperature effect still remains.

In an application where errors on this level are allowed for the absolute humidity AH, AH may be calculated from the characteristics shown in FIG. 12. For example, when accurate values of humidity are not required in such a case as humidity measurement for air conditioner control within the vehicle compartment, this method can be employed. However, in an application where high accuracy is required in such a case as airflow amount control for the fuel cell system, variations in AH due to temperature change need to be corrected.

For increasing accuracy in the absolute humidity AH, it is now considered that a function of temperature is introduced into Hum in FIG. 12 to find a function which allows the plots to be apparently positioned on a single correction curve. As one of easy methods, a conversion table showing correction values for each temperature is prepared, and the table is stored in a memory and referred to based on temperature data. In this method, however, a correction curve corresponding to each temperature needs to be obtained. This process is extremely complicated during mass production of gas sensors and requires a great volume of memory, which raises cost.

In the gas sensor in the embodiment according to the invention, various methods of introducing a temperature function were examined, and the fact were found that the highest correction accuracy can be obtained when a correlation between the absolute humidity AH and a value obtained by multiplying Hum by the cubed reciprocal of T indicating temperature is plotted. It was also confirmed that the calculation by this method increases accuracy in AH to the highest from the above thermal conductivity theoretical equation. Since the thermal conductivity theoretical equation is used, the volume of memory required for the gas sensor can be decreased and therefore the cost can be reduced.

Figure 13:
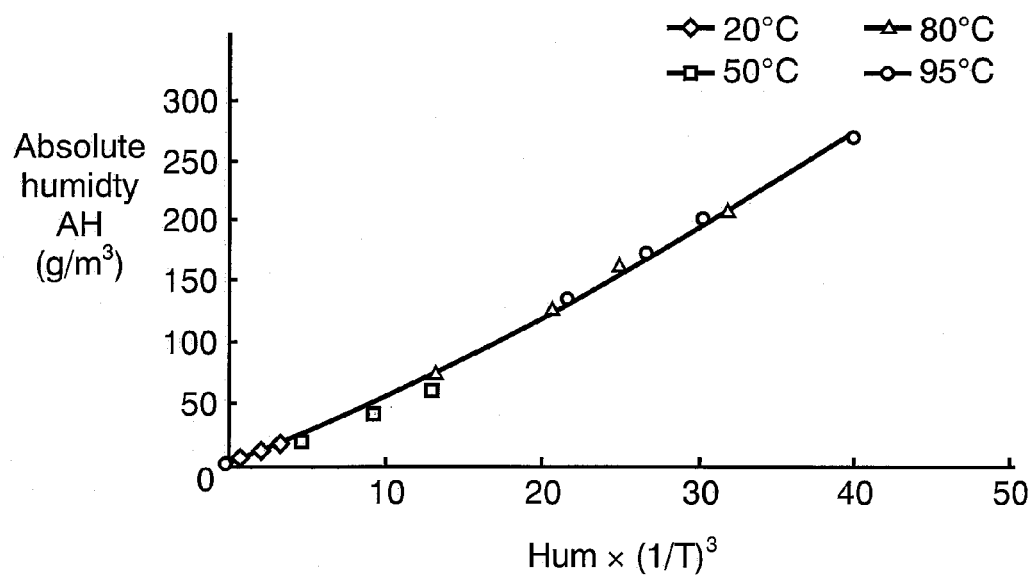
FIG. 13 shows a correlation between the absolute humidity and a value obtained by multiplying the difference between the standardized outputs by the cubed reciprocal of the both-end voltage of the heating element when the lowest current flows in the gas sensor in the embodiment according to the invention.

The results obtained through this correction are shown in FIG. 13. FIG. 13 represents a correlation between the absolute humidity AH and a value obtained by multiplying the difference between the standardized outputs by the cubed reciprocal of the both-end voltage of the heating element when the lowest current flows in the gas sensor in the embodiment according to the invention. In the figure, the horizontal axis indicates $Hum \times (1/T)^3$, while the vertical axis indicates the absolute humidity AH. As can be seen from FIG. 13, the plot at each temperature is positioned substantially on a single correction curve even when temperature varies. This means higher accuracy in the absolute humidity AH. The following equation is a calculation (humidity correlation function) which cubicly approximates the correlation between the absolute humidity AH and the multiplied value using the method of least squares:

$$AH = -0.0027 \times (Hum/T^3)^3 + 0.1935 \times (Hum/T^3)^2 + 3.1025 \times Hum/T^3 + 0.7809 \qquad (9)$$

Thus, the absolute humidity AH can be obtained by substituting the parameters of the difference Hum between the standardized outputs and T corresponding to the ambient temperature (both-end voltage of the heating element when the lowest current flows) in the humidity correlation function (9). Since cubic approximation is employed, the correction errors can be decreased compared with the case when lower-degree approximation is used.

While AH in the unit of absolute humidity is obtained in this embodiment, relative humidity may be calculated from AH and T using known formulae or the like.

Next, the method of calculating hydrogen concentration is discussed.

As obvious from FIG. 8, humidity can be corrected by subtracting offset from the sensor output. Since the offset varies in accordance with humidity change, the correlation between Hum indicating humidity and offset is required before execution of humidity correction. The correlation obtained is shown in FIG. 14.

Figure 14:
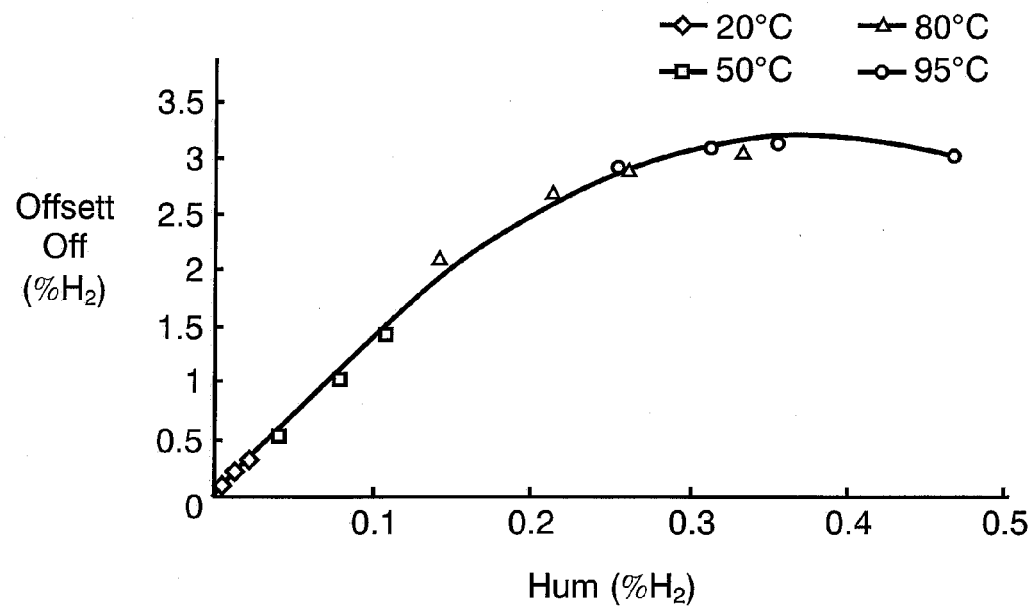
FIG. 14 shows a correlation between offset and the difference between the standardized outputs in the gas sensor in the embodiment according to the invention.

FIG. 14 represents the correlation between the offset and the difference between the standardized outputs in the gas sensor in the embodiment according to the invention. In the figure, the horizontal axis indicates Hum, while the vertical axis indicates offset Off obtained from FIG. 8. Based on FIG. 14, it is possible to determine one value as the offset Off which is to be subtracted from the sensor output relative to Hum. Practically, the offset Off can be calculated by substituting Hum in the relational equation of the approximate curve showing Hum and the offset Off obtained from the respective plots in FIG. 14 using the method of least squares. Then, hydrogen output Out is obtained by subtracting the offset Off from the standardized output KH.

Figure 15:
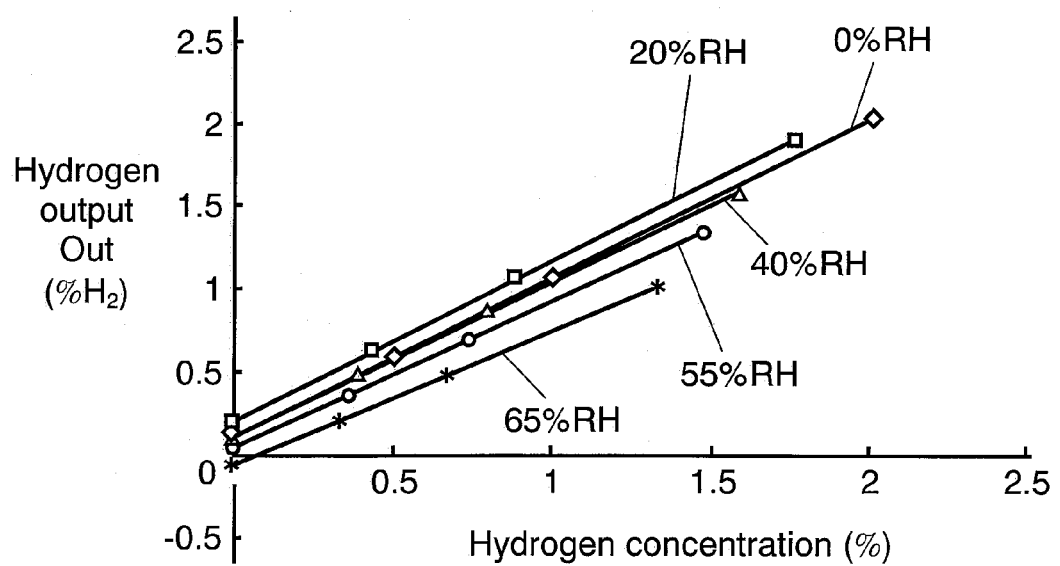
FIG. 15 shows hydrogen concentration output characteristics in a humidified condition after humidity correction shown in FIG. 14 in the gas sensor in the embodiment according to the invention.

The results practically obtained after correction of FIG. 8 through the calculation by this method are shown in FIG. 15. FIG. 15 represents hydrogen concentration output characteristics under a humidified condition after humidity correction by the method in FIG. 14 in the gas sensor in the embodiment according to the invention. In FIG. 15, the horizontal axis indicates hydrogen concentration contained in the detection target gas, while the vertical axis indicates the hydrogen output Out. The offset which is extremely large in FIG. 8 can be greatly decreased. However, it is obvious that the zero-point accuracy is insufficient. Further detailed examination shows the fact that the hydrogen concentration sensitivity (inclination) varies in accordance with humidity change.

When the offset Off is calculated from Hum and the humidity correction is performed in this condition, the hydrogen concentration errors increase. This is because the difference between the respective plots and the approximate curve is great also in FIG. 15 as discussed referring to FIG. 12.

When investigating the characteristics of the plot at each temperature also in FIG. 14, the respective plots are positioned substantially on the same curve at a constant temperature. Accordingly, the correlation between Hum and the offset Off varies as temperature changes, and therefore the correction cannot be performed based on a single correction curve. Similar results are obtained when variations in Hum and the thermal conductivity (corresponding to the offset Off) in accordance with temperature change are calculated using the above thermal conductivity theoretical equation. This means that the temperature effect still remains.

It is therefore necessary to further correct these variations in accordance with temperature change in applications for securing safety such as detection of hydrogen leak in the fuel cell system.

As mentioned earlier referring to FIG. 12, for performing temperature correction with high accuracy, it is necessary to introduce a temperature function into Hum in FIG. 14 and find such a function that allows the respective plots to be apparently positioned on a single correction curve.

Based on the above viewpoints, the inventor of the invention investigated various methods of introducing a temperature function, and found that the correction accuracy increases to the highest when plotting a correlation between the offset Off and a value obtained by multiplying Hum by cubed T indicating temperature. It was also confirmed that the highest accuracy of the offset Off can be obtained when this calculation is employed from the thermal conductivity theoretical equation.

Figure 16:
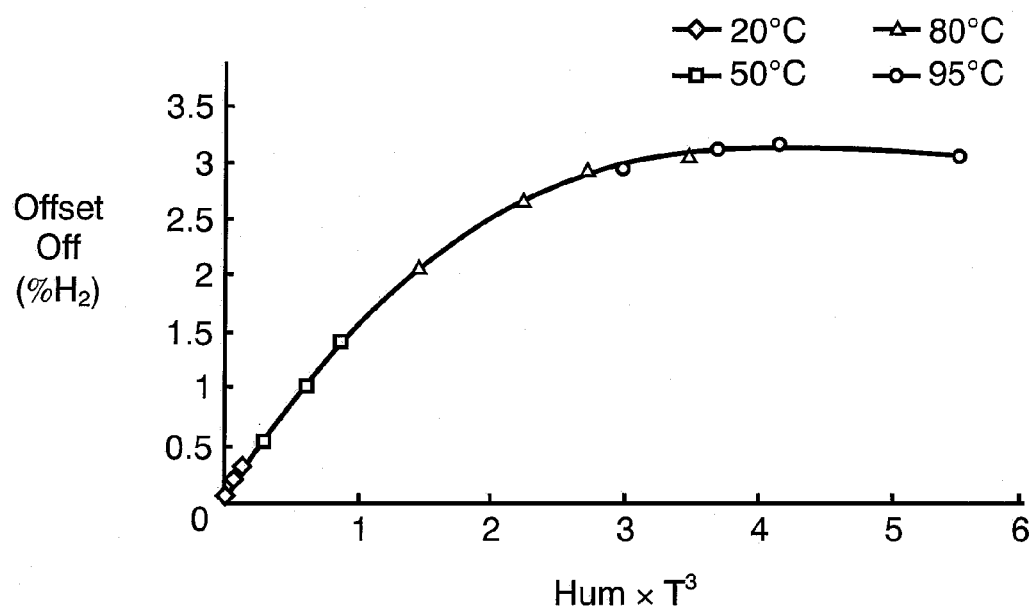
FIG. 16 shows a correlation between the offset and the value obtained by multiplying the difference between the standardized outputs by the cubed reciprocal of the both-end voltage of the heating element when the lowest current flows in the gas sensor in the embodiment according to the invention.

The results obtained through this correction are shown in FIG. 16. FIG. 16 represents a correlation between the offset Off and a value obtained by multiplying the difference between the standardized outputs by the cubed reciprocal of the both-end voltage of the heating element when the lowest current flows in the gas sensor in the embodiment according to the invention. In the figure, the horizontal axis indicates $Hum \times T^3$, while the vertical axis indicates the offset Off. As can be seen from FIG. 16, the plot at each temperature is positioned substantially on a single correction curve even when temperature varies. This means higher accuracy in the offset Off. The following equation is a calculation (first humidity correction value correlation function for zero-point fluctuation correction) which cubicly approximates the correlation between the offset Off and the multiplied value using the method of least squares:

$$Off = -0.0244 \times (Hum \times T^3)^3 - 0.38 \times (Hum \times T^3)^2 + 1.9029 \times Hum \times T^3 + 0.0389 \quad (10)$$

Thus, the offset Off can be obtained by substituting the parameters of the difference between the standardized outputs Hum and T corresponding to the ambient temperature (both-end voltage of the heating element when the lowest current flows) in the first humidity correction value correlation function for zero-point fluctuation correction (10). Since cubic approximation is employed, the correction errors can be decreased compared with the case when lower-degree approximation is used.

Thus, the hydrogen output Out after humidity correction can be obtained from the following equation:

$$Out = KH - Off \quad (11)$$

Basically, the hydrogen output Out indicating the concentration output containing only hydrogen can be obtained from the above calculations. In reality, however, heating element 1 very slightly generates heat at the time of measurement of T corresponding to the ambient temperature as current of 1 mA flows through heating element 1. As a result, T has slight humidity sensitivity and hydrogen sensitivity. Accordingly, the inclination (=hydrogen sensitivity) of the hydrogen output Out varies in accordance with humidity change as shown in FIG. 15. When correction calculation according to the equations (1) through (11) is performed in this condition, errors are caused in the hydrogen output Out.

Figure 17:
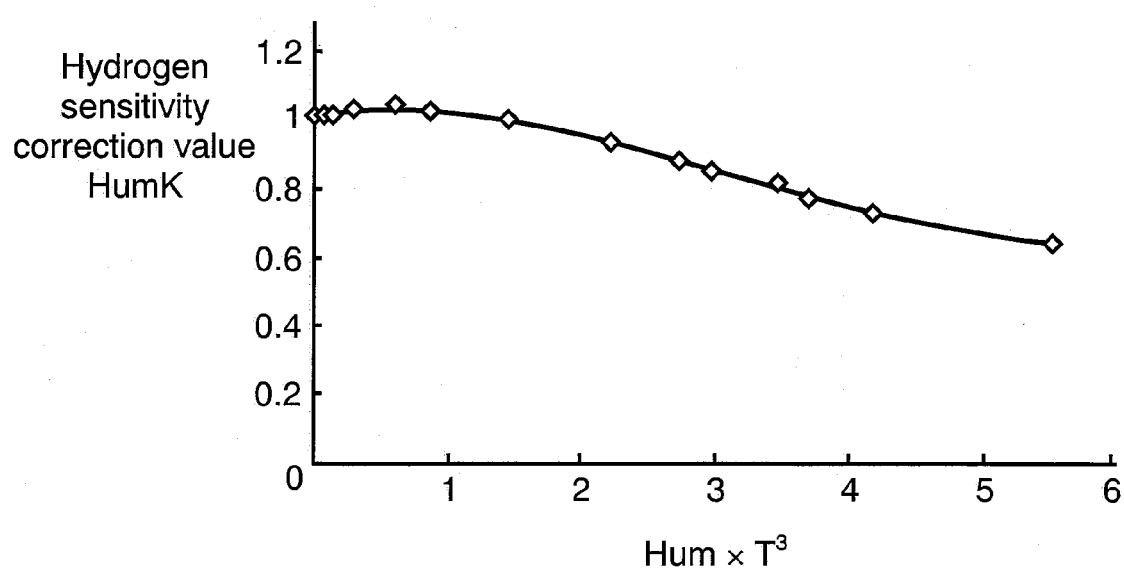
FIG. 17 shows a correlation between a hydrogen sensitivity correction value and a value obtained by multiplying the difference between the standardized outputs by the cubed both-end voltage of the heating element when the lowest current flows in the gas sensor in the embodiment according to the invention.

For reducing these sensitivity errors, hydrogen sensitivity correction value HumK is obtained for each humidity. HumK herein indicates the inclination for each humidity in FIG. 15. FIG. 17 represents how HumK correlates with $Hum \times T^3$ corresponding to humidity. FIG. 17 shows a correlation between the hydrogen sensitivity correction value and a value obtained by multiplying the difference between the standardized outputs by the cubed both-end voltage of the heating element when the lowest current flows in the gas sensor in the embodiment according to the invention. In FIG. 17, the horizontal axis indicates $Hum \times T^3$, while the vertical axis indicates the hydrogen sensitivity correction value HumK.

As can be seen from FIG. 17, HumK decreases to lower than 1 as $Hum \times T^3$ (corresponding to humidity) increases. That is, the inclination (hydrogen concentration sensitivity) in the graph in FIG. 15 decreases. Thus, by correcting the inclination according to humidity based on the correlation, the hydrogen sensitivity is equalized at any humidity, and therefore the accuracy of gas sensor can be increased.

The correlation for each plot is obtained as a calculation (second humidity correction value correlation function for sensitivity fluctuation correction) which cubicly approximates using the method of least squares. The resultant correlation is expressed by the following equation:

$$HumK = 0.0054 \times (Hum \times T^3)^3 - 0.0517 \times (Hum \times T^3)^2 + 0.0581 \times Hum \times T^3 + 1.0088 \quad (12)$$

Thus, HumK can be obtained by substituting the parameters of the difference Hum between the standardized outputs and T corresponding to the ambient temperature (both-end voltage of the heating element when the lowest current flows) in the second humidity correction value correlation function for sensitivity fluctuation correction (12). Since cubic approximation is employed, the correction errors can be decreased compared with the case when lower-degree approximation is used.

Accordingly, final hydrogen concentration output H2 after sensitivity correction can be calculated using the following equation:

$$H2 = Out/Humk \quad (13)$$

Figure 18:
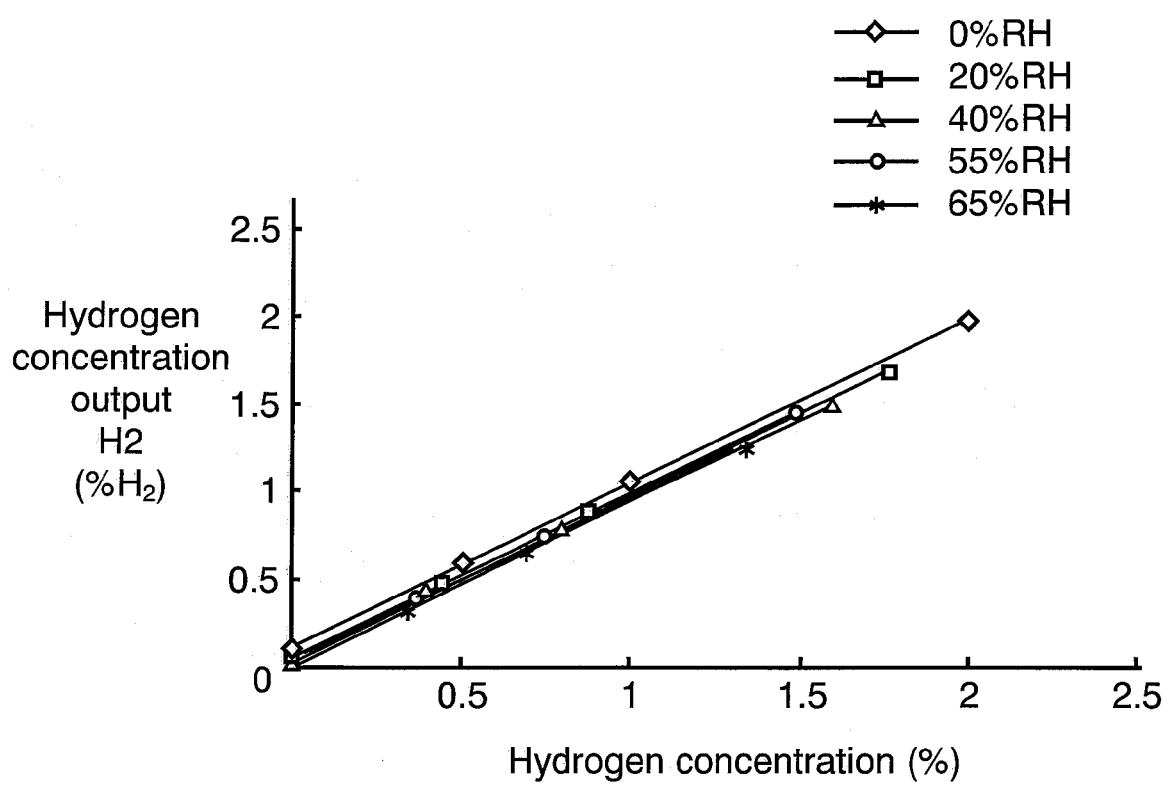
FIG. 18 shows hydrogen concentration output characteristics in a humidified condition after humidity correction shown in FIGS. 16 and 17 in the gas sensor in the embodiment according to the invention.

The resultant values of the hydrogen concentration output H2 obtained through the above calculations are shown in FIG. 18. FIG. 18 represents hydrogen concentration output characteristics under a humidified condition after humidity correction shown in FIGS. 16 and 17. In FIG. 18, the horizontal axis indicates the hydrogen concentration of the detection target gas, while the vertical axis indicates the hydrogen concentration output H2 as sensor output after correction. In this figure, zero-point errors and sensitivity errors are greatly reduced compared with the case in FIG. 15, and a gas sensor having high accuracy of $\pm 0.1\%$ $H_2$ is obtained.

Accordingly, the gas sensor according to the invention can simultaneously detect humidity and hydrogen concentration with extremely high precision by performing the correction calculations (1) through (13).

Since all the calculations (1) through (13) are constituted by easy four basic operations of arithmetic, a highly responsive gas sensor can be realized which is more accurate and performs calculations at extremely higher speed than a conventional gas sensor which calculates simultaneous equations quadratic or having higher degrees and obtains a plurality of solutions. Thus, the calculation method in this embodiment is highly appropriate for such systems that are easily affected by humidity.

Figure 19:
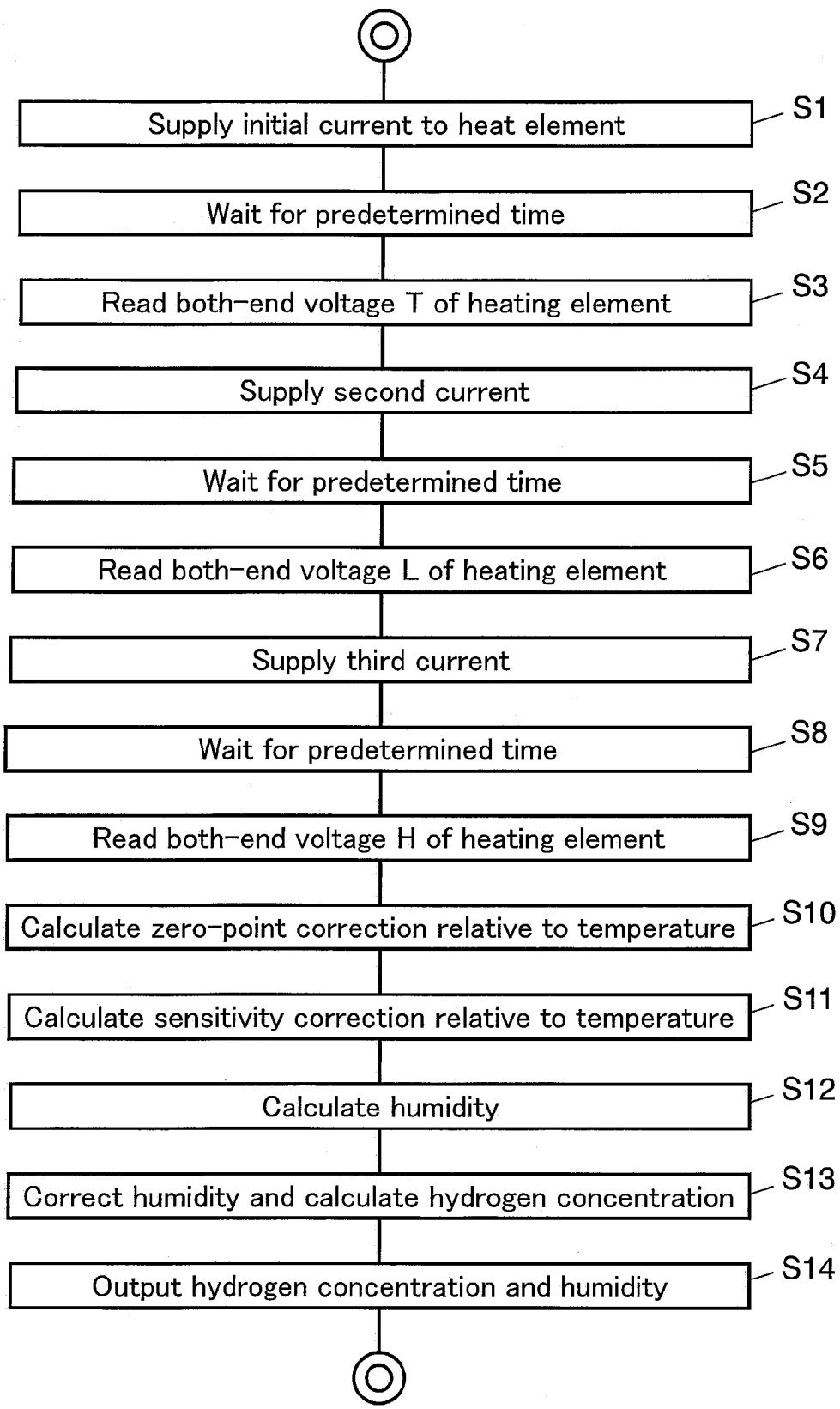
FIG. 19 is a flowchart showing procedures for calculating hydrogen concentration and humidity in the gas sensor in the embodiment according to the invention.

This calculation method is programmed in arithmetic unit 27. When the output values T, L and H obtained from heating element 1 during operation of the gas sensor are inputted to arithmetic unit 27, arithmetic unit 27 performs the calculations (1) through (13) and outputs humidity and hydrogen concentration. Sub routines of the calculation procedures are shown in a flowchart in FIG. 19. Thus, FIG. 19 is a flowchart showing the processes of calculating the hydrogen concentration and humidity outputted from the gas sensor in the embodiment according to the invention.

First, initial current (herein 1 mA) is supplied to heating element 1 (S1). After elapse of predetermined time (0.1 second) (S2), the both-end voltage T of heating element 1 is read (S3). Then, second current (herein 7 mA) is supplied to heating element 1 (S4). After elapse of predetermined time (0.1 second) (S5), the both-end voltage T of heating element 1 is read (S6). Similarly, third current (herein 7.5 mA) is supplied to heating element 1 (S7). After elapse of predetermined time (0.1 second) (S8), the both-end voltage H of heating element 1 is read (S9). Then, current supply to heating element 1 is stopped. Next, zero-point correction calculation relative to temperature is performed using the equations (1) through (4) (S10), and then sensitivity correction calculation relative to temperature is performed based on the results obtained in S10 using the equations (5) through (8) (S11). Subsequently, humidity is calculated using the equation (9) (S12). Thereafter, humidity correction is performed using the equations (10) through (13) to calculate the hydrogen concentration (S13). Finally, the hydrogen concentration and humidity are outputted (S14). These processes constituting one cycle are repeated so that the hydrogen concentration and humidity can be continuously outputted. Accordingly, the hydrogen concentration and humidity can be monitored with elapse of time by repeating this detection.

While only the hydrogen concentration and humidity are outputted in this embodiment, the ambient temperature based on T value may be outputted as necessary.

By employing the above structure and operation, a gas sensor can be obtained which is capable of separately detecting hydrogen concentration and humidity with high accuracy under the environment of co-existing hydrogen and vapor. While the case where vapor and hydrogen co-exist has been discussed in this embodiment, gas concentration can be outputted by a similar method in case of combinations of gases other than hydrogen.

INDUSTRIAL APPLICABILITY

As described above, a gas sensor according to the invention includes a heating element which contacts detection target gas mixed with the atmosphere containing moisture, a power source device for supplying electric current to the heating element, and a voltmeter for measuring voltage at both ends of the heating element. The gas sensor further includes an arithmetic unit for calculating humidity and the concentration of the detection target gas based on the output voltage and outputting the calculated values. The arithmetic unit commands the power source device to supply at least three levels of current to the heating element successively in a step-like manner for a predetermined time period. Then, the arithmetic unit receives the both-end voltages of the heating element for the respective current after elapse of the predetermined time period. Thereafter, the arithmetic unit corrects the both-end voltages of the heating element obtained when current other than the lowest current flow using a zero-point fluctuation correcting equation and a sensitivity fluctuation correcting equation obtained in advance based on the both-end voltage of the heating element when the lowest current flows and a known concentration of the detection target gas so as to obtain respective standardized output values. Subsequently, the arithmetic unit calculates humidity using a humidity correlation function which uses parameters of the difference between the standardized output values and the both-end voltage of the heating element when the lowest current flows. Thereafter, the arithmetic unit corrects the zero-point fluctuation and sensitivity fluctuation relative to the humidity thus obtained using two humidity correction value correlation functions which use parameters of the difference between the standardized output values and the both-end voltage of the heating element when the lowest current flows to obtain the concentration of the detection target gas. By this method, the gas sensor according to the invention can detect humidity and concentration of detection target gas with high accuracy.

Accordingly, the gas sensor according to the invention is appropriately used particularly for such an application as humidity and hydrogen leak detection in a fuel cell system which maybe be exposed to high temperature and high humidity environment.

The invention claimed is:

1. A gas sensor, comprising:
 a heating element which contacts a detection target gas mixed with the atmosphere containing moisture;
 a power source device for supplying electric current to the heating element; and
 an arithmetic unit for calculating humidity and concentration of the detection target gas based on output voltage from a voltmeter and outputting the calculated values, the arithmetic unit configured to calculate the concentration of the detection target gas by performing the steps of:
  A) commanding the power source device to supply at least a first current, a second current and a third current, the second and third current of which are larger than the first current, to the heating element successively in a step-like and sequential manner for a predetermined time period;
  B) receiving from the voltmeter a first output value, a second output value and a third output value as the both-end voltages of the heating element for the first current, the second current and the third current, respectively, after elapse of the predetermined time period;
  C) obtaining the ambient temperature from the first output value wherein the first output value proportional to the ambient temperature;
  D) correcting the second output value and the third output value using an equation for correcting the second output value and the third output value based on the obtained ambient temperature and a zero-point output given from the voltmeter when only dry air exists and an equation for correcting sensitivity of the heating element obtained in advance based on a known concentration of the detection target gas so as to obtain a first standardized output value for the second current and a second standardized output value for the third current;

E) calculating humidity using a humidity correlation function which uses parameters of the first output value and a difference between the first standardized output value and the second standardized output value; and F) correcting zero-point fluctuation relative to the humidity obtained in step E) using a first humidity correction value correlation function which uses parameters of the first output value and the difference between the first standardized output value and the second standardized output value, and correcting sensitivity fluctuation relative to the humidity obtained in step E) using a second humidity correction value correlation function which uses parameters of the first output value and the difference between the first standardized output value and the second standardized output value.

2. The gas sensor of claim 1, wherein the arithmetic unit is configured to repeat the steps of A) through F).

3. The gas sensor of claim 1, wherein the first current is 1 mA or lower.

4. The gas sensor of claim 1, wherein the parameters given to the humidity correlation function are calculated by multiplying the difference between the first standardized output value and the second standardized output value by the reciprocal of the first output value raised to a higher power.

5. The gas sensor of claim 4, wherein the reciprocal of the first output value is raised to the third power.

6. The gas sensor of claim 1, wherein the humidity correlation function is expressed by a cubic equation.

7. The gas sensor of claim 1, wherein a value obtained by multiplying the difference between the first standardized output value and the second standardized output value by the first output value raised to a higher power is used as a parameter for the first humidity correction value correlation function and the second humidity correction value correlation function.

8. The gas sensor of claim 7, wherein the first output value is raised to the third power.

9. The gas sensor of claim 1, wherein each of the first humidity correction value correlation function and the second humidity correction value correlation function is expressed by a cubic equation.

10. The gas sensor of claim 1, wherein the heating element includes: a pedestal made of silicone; an insulating layer provided on the pedestal; a heating body provided on the insulating layer; and a concavity formed below the insulating layer of the pedestal equipped with the heating body.

11. The gas sensor of claim 1, wherein the heating element has platinum thin film.

12. A fuel cell system, comprising: the gas sensor of claim 1 for outputting hydrogen concentration; a fuel cell for generating electricity using fuel of hydrogen; and a control circuit for stopping hydrogen supply to the fuel cell when an output indicating hydrogen from the gas sensor exceeds a predetermined value.

13. The fuel cell system of claim 12, further comprising: a flow path through which hydrogen is supplied to the fuel cell; and a ventilator for ventilating a space including the flow path, wherein: the control circuit controls the ventilator such that the ventilator ventilates the space when an output indicating hydrogen from the gas sensor exceeds the predetermined value.

14. The fuel cell system of claim 13, further comprising: an air compressor connected with the fuel cell; an air humidifier connected with the air compressor; and a discharge passage through which air is discharged from the fuel cell, wherein: the air compressor is controlled such that the air amount discharged through the discharge passage increases when the gas sensor detects that the hydrogen concentration within the discharge passage exceeds a predetermined value; and the air humidifier is controlled such that a predetermined humidity can be maintained based on a humidity output obtained by through detection of the gas sensor.

15. The fuel cell system of claim 12, further comprising: an air compressor connected with the fuel cell; an air humidifier connected with the air compressor; and a discharge passage through which air is discharged from the fuel cell, wherein: the air compressor is controlled such that the air amount discharged through the discharge passage increases when the gas sensor detects that the hydrogen concentration within the discharge passage exceeds a predetermined value; and the air humidifier is controlled such that a predetermined humidity can be maintained based on a humidity output obtained by through detection of the gas sensor.

16. An automobile, comprising: a main body forming a vehicle compartment; tires for supporting the main body; a motor for driving the tires; a fuel cell for generating electricity using fuel of hydrogen and for supplying electric power to the motor; the gas sensor of claim 1 disposed in the upper region of the vehicle compartment to output hydrogen concentration; and a control circuit for stopping hydrogen supply to the fuel cell when an output indicating hydrogen from the gas sensor exceeds a predetermined value.

17. The automobile of claim 16, further comprising a ventilator which is so controlled as to ventilate a space provided within the main body by the control circuit when an output indicating hydrogen from the gas sensor exceeds the predetermined value.

18. The automobile of claim 16, further comprising an alarm which is so controlled as to give a warning by the control circuit when an output indicating hydrogen from the gas sensor exceeds the predetermined value.

19. The automobile of claim 16, further comprising an air conditioner for controlling humidity in the vehicle compartment, wherein: the control circuit controls the air conditioner such that humidity in the vehicle compartment can be optimized based on humidity output from the gas sensor.

* * * * *